US00PP20040P2

(12) United States Plant Patent
Wood

(10) Patent No.: US PP20,040 P2
(45) Date of Patent: Jun. 2, 2009

(54) ***WEIGELA* PLANT NAMED 'DV PUTTEN'**

(50) Latin Name: *Weigela florida*
Varietal Denomination: DV Putten

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/075,452

(22) Filed: Mar. 11, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—S. B McCormick Ewoldt
(74) *Attorney, Agent, or Firm*—C. A. Whealy

(57) ABSTRACT

A new and distinct cultivar of *Weigela* plant named 'DV Putten', characterized by its compact and uniform plant habit; freely branching habit; dark green and yellow green variegated foliage; light pink-colored flowers; and good garden performance.

2 Drawing Sheets

Botanical designation: *Weigela florida.*
Cultivar denomination: 'DV PUTTEN'.

BACKGROUND OF THE INVENTION

The present invention relates to a new and distinct cultivar of *Weigela* plant, botanically known as *Weigela florida,* and hereinafter referred to by the name 'DV Putten'.

The new *Weigela* is a product of a planned breeding program conducted by the Inventor in Grand Haven, Mich. The objective of the breeding program was to develop new *Weigelas* with unique leaf shapes and coloration, uniform plant habit and hardiness.

The new *Weigela* originated from a cross-pollination of two unidentified selections of *Weigela florida,* not patented. The cultivar DV Putten was discovered and selected by the Inventor in 2002 as a flowering plant within the progeny of the stated cross-pollination in a controlled environment in Grand Haven, Mich. Asexual reproduction of the new cultivar by cuttings in Grand Haven, Mich. since 2004 has shown that the unique features of this new *Weigela* plant are stable and reproduced true to type in successive generations of asexual reproduction.

SUMMARY OF THE INVENTION

The following traits have been repeatedly observed and are determined to be the unique characteristics of 'DV Putten'. These characteristics in combination distinguish 'DV Putten' as a new and distinct cultivar of *Weigela:*

1. Compact and uniform plant habit.
2. Freely branching habit.
3. Dark green and yellow green variegated foliage.
4. Light pink-colored flowers.
5. Good garden performance.

In side-by-side comparisons in Grand Haven, Mich., under commercial practice, plants of the new *Weigela* differ from plants of the parent selections primarily in leaf color as plants of the parent selections do not have variegated leaves.

Plants of the new *Weigela* can be compared to plants of the *Weigela florida* cultivar Gold Rush, not patented. In side-by-side comparisons in Grand Haven, Mich. plants of the new *Weigela* differ from plants of the cultivar Gold Rush in the following characteristics:

1. Plants of the new *Weigela* are more compact than plants of the cultivar Gold Rush.
2. Plants of the new *Weigela* have brownish red-colored stems whereas plants of the cultivar Gold Rush have green-colored stems.
3. Plants of the new *Weigela* and the cultivar Gold Rush differ in leaf coloration as plants of the cultivar Gold Rush larger areas of dark green on the leaves.

BRIEF DESCRIPTION OF THE PHOTOGRAPHS

The accompanying colored photographs illustrate the overall appearance of the new *Weigela,* showing the colors as true as it is reasonably possible to obtain in colored reproductions of this type. Colors in the photographs may differ slightly from the color values cited in the detailed botanical description which accurately describe the colors of the new *Weigela.*

The photograph on the first sheet comprises a side perspective view of a typical plant of the cultivar DV Putten.

The photograph at the top of the second sheet is a close-up view of typical flowers of the cultivar DV Putten.

The photograph at the bottom of the second sheet is a close-up view of typical leaves of the cultivar DV Putten.

DETAILED BOTANICAL DESCRIPTION

The new *Weigela* has not been observed under all possible environmental conditions. The phenotype may vary somewhat with variations in environment such as temperature and light intensity, without, however, any variance in genotype. The aforementioned photographs, following observations and measurements describe plants grown during the spring and early summer in Grand Haven, Mich., in an outdoor nursery and under commercial production practices. Plants were about three years old when the photographs and description were taken. In the following description, color references are made to The Royal Horticultural Society Colour Chart, 1995 Edition, except where general terms of ordinary dictionary significance are used.

Botanical classification: *Weigela florida* cultivar DV Putten.

Parentage:

*Female or seed, parent.*—Unidentified selection of *Weigela florida,* not patented.

*Male or pollen, parent.*—Unidentified selection of *Weigela florida,* not patented.

Propagation:

*Type.*—By softwood cuttings.

*Time to initiate roots.*—About 15 days at temperatures of 22° C.

*Time to produce a rooted young plant.*—About two months at temperatures of 22° C.

*Root description.*—Mostly fine.

*Rooting habit.*—Freely branching; dense.

Plant description:

*Plant and growth habit.*—Perennial shrub. Compact and uniform plant habit; roughly spherical in shape. Vigorous growth habit. Freely branching habit with about 18 lateral branches developing per plant; pinching enhances lateral branch development.

*Plant height.*—About 1 meter.

*Plant diameter.*—About 1 meter.

Lateral branch description:

*Length.*—About 40 cm.

*Diameter.*—About 4 mm.

*Internode length.*—About 5 cm.

*Strength.*—Strong.

*Aspect.*—Erect to about 40° from vertical.

*Texture.*—Pubescent.

*Color, developing stems.*—178A.

*Color, mature stems.*—197B.

Foliage description:

*Arrangement.*—Opposite; simple.

*Length.*—About 8 cm.

*Width.*—About 4.5 cm.

*Shaped.*—Elliptic to ovate.

*Apex.*—Acute to acuminate.

*Base.*—Cuneate.

*Margin.*—Serrulate; slightly undulating.

*Texture, upper surface.*—Smooth, glabrous.

*Texture, lower surface.*—Smooth, pubescence at veins.

*Venation pattern.*—Pinnate.

*Color.*—Developing foliage, upper surface: Center, 143A; towards the margins, 144D, occasionally speckled with close to 60A. Developing foliage, lower surface: Center, 143B; towards the margins, 144D. Fully expanded foliage, upper surface: Center, between 139A and 137A; towards the margins, between 143B to 144B; venation, 144B. Fully expanded foliage, lower surface: Center, 138A to 138B; towards the margins, between 143A to 145B; venation, 150D.

*Petiole.*—Length: About 6 mm. Diameter: About 4 mm. Texture, upper and lower surfaces: Smooth, glabrous. Color, upper and lower surfaces: 144B.

Flower description:

*Flower arrangement and habit.*—Funnelform flowers arranged in clusters of about seven flowers. Flowers not persistent. Flowers face upright, outwardly or are drooping.

*Fragrance.*—None detected.

*Natural flowering season.*—Plants of the new *Weigela* flower from May to June in Grand Haven, Mich.

*Flower longevity.*—Flowers last about six to eight weeks on the plant.

*Flower diameter.*—About 2.5 cm.

*Flower length (height).*—About 3.5 cm.

*Flower bud.*—Shape: Narrowly ovate. Length: About 1.5 cm. Diameter: About 5 mm. Color: 58A.

*Corolla.*—Arrangement: Funnelform, five petals fused into a long tube with separate petal lobes. Petal lobe length: About 1.2 cm. Petal lobe width: About 1 cm. Petal lobe shape: Roughly orbicular. Petal lobe apex: Obtuse. Petal lobe margin: Entire. Petal texture, upper and lower surfaces: Smooth, glabrous. Color: Petal, when opening, upper surface: 74C. Petal, when opening, lower surface: 74B. Petal, fully opened, upper surface: 74D; color becoming closer to 155D with development. Petal, fully opened, lower surface: 74C.

*Sepals.*—Quantity per flower: Five. Length: About 9 mm. Width: About 0.5 mm to 1 mm. Shape: Lanceolate. Apex: Acuminate. Margin: Entire. Sepal texture, upper and lower surfaces: Smooth; glabrous. Color, upper and lower surfaces: 177C.

*Peduncles.*—Length: About 2 cm. Diameter: About 2 mm. Angle: Erect to about 30° from stem axis. Strength: Moderately strong; flexible. Texture: Smooth, glabrous. Color: 146A.

*Pedicels.*—Length: About 1.2 cm. Diameter: About 1.5 mm. Angle: About 20° from stem axis. Strength: Moderately strong; flexible. Texture: Smooth, glabrous. Color: 178A.

*Reproductive organs.*—Stamens: Quantity/arrangement: Five per flower. Anther shape: Oblong. Anther length: About 5 mm. Anther color: 196A. Pollen amount: Moderate. Pollen color: 196A. Pistils: Quantity: One per flower. Pistil length: About 2.9 cm. Style length: About 2.5 cm. Style color: 196C. Stigma color: 196C. Seeds: Length: Less than 0.5 mm. Diameter: Less than 0.5 mm. Color: Close to 200A.

Garden performance: Plants of the new *Weigela* have exhibited good tolerance to rain and wind and have been observed to tolerate temperatures from about −29° C. to about 38° C.

Pathogen/pest resistance: Plants of the new *Weigela* have not been observed to be resistant to pests and pathogens common to *Weigela.*

It is claimed:

1. A new and distinct *Weigela* plant named 'DV Putten' as illustrated and described.

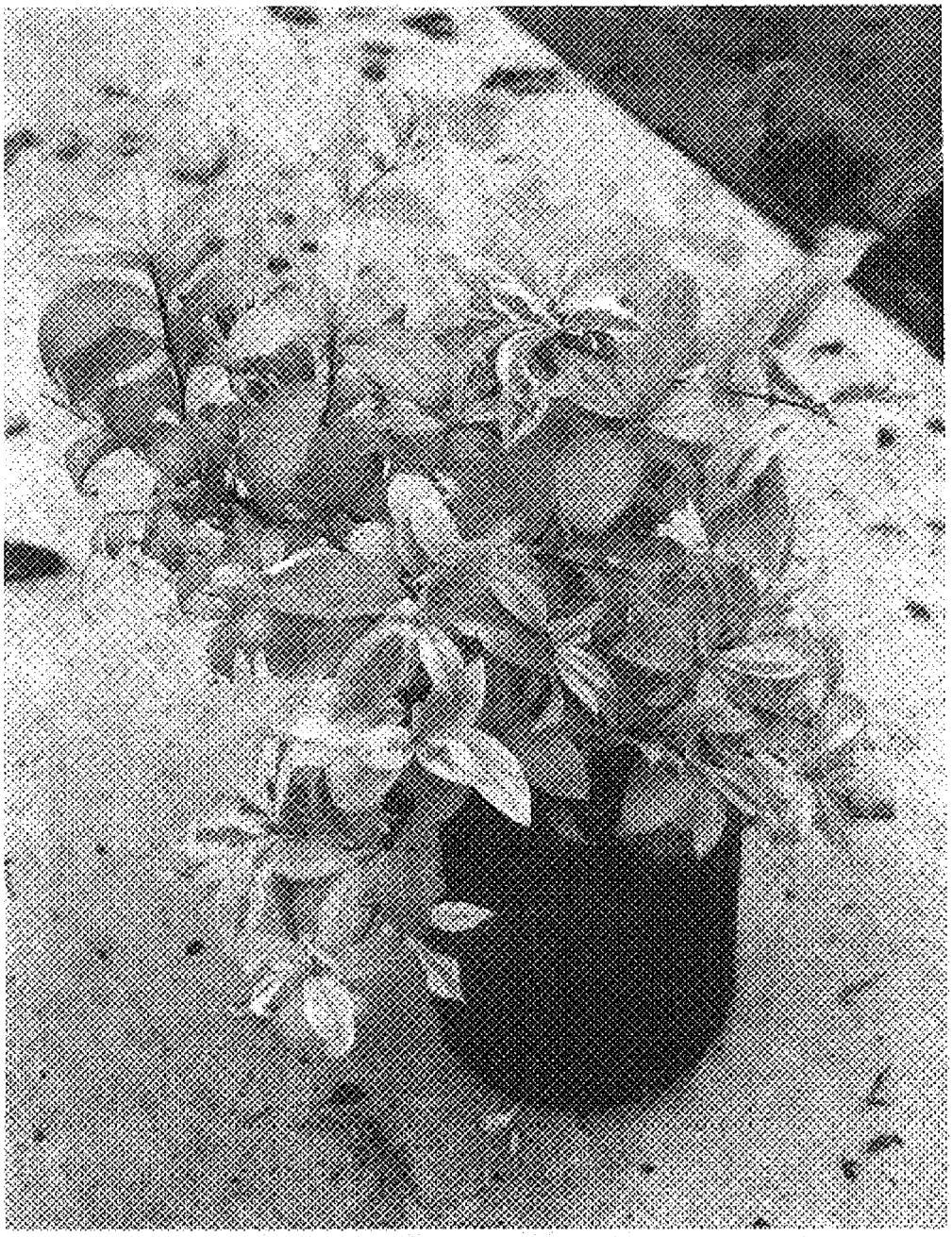

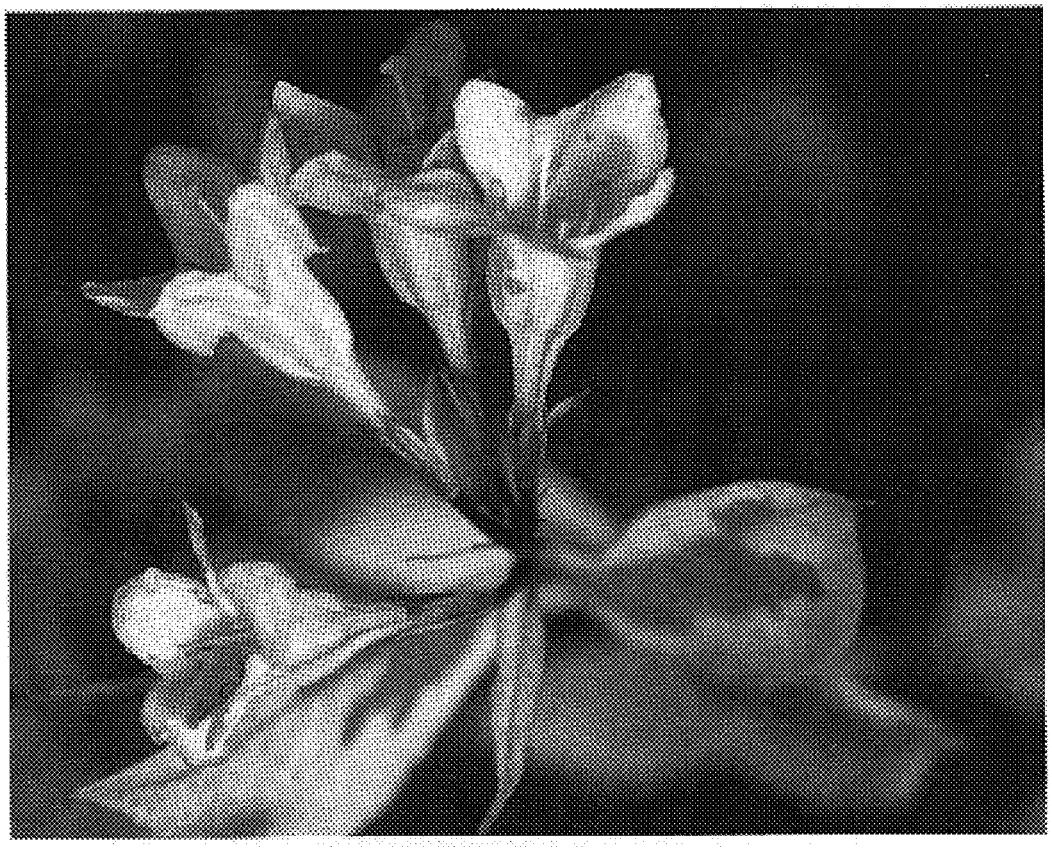
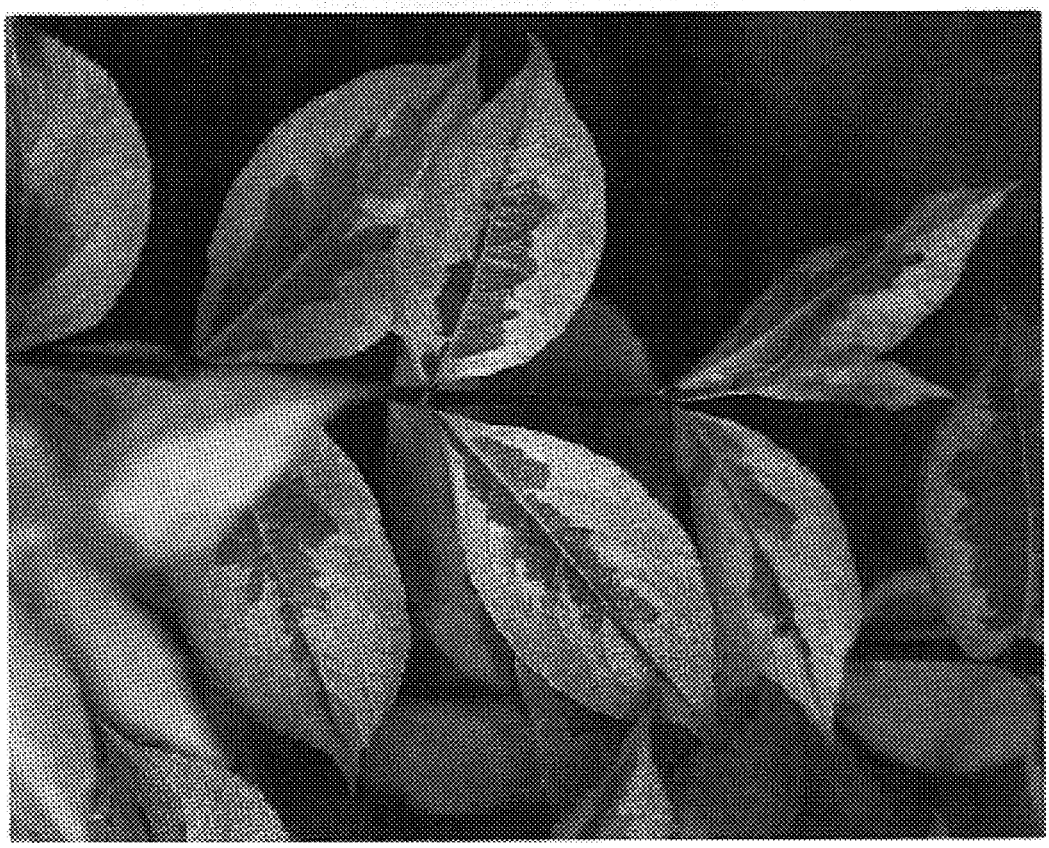

* * * * *